United States Patent [19]
Braswell et al.

[11] Patent Number: 6,132,712
[45] Date of Patent: Oct. 17, 2000

[54] SUPEROXIDE DISMUTASE STABILIZED WITH FRAGMENTS OF CASEIN AND PHARMACEUTICAL COMPOSITIONS INCORPORATING SAME

[75] Inventors: A. Glenn Braswell, Suite 420, 520 Washington Blvd., Marina Del Rey, Calif. 90292; Aftab J. Ahmed, Marina Del Rey, Calif.

[73] Assignee: A. Glenn Braswell, Atlanta, Ga.

[21] Appl. No.: 08/989,159

[22] Filed: Dec. 11, 1997

(Under 37 CFR 1.47)

Related U.S. Application Data
[60] Provisional application No. 60/032,396, Dec. 11, 1996.

[51] Int. Cl.⁷ .......................... A61K 38/54; A61K 38/44; C12N 9/96; C12N 9/02
[52] U.S. Cl. ...................... 424/94.3; 424/94.4; 435/188; 435/189
[58] Field of Search .................... 435/189, 188; 424/94.4, 94.3

[56] References Cited

U.S. PATENT DOCUMENTS

| | | | |
|---|---|---|---|
| 3,637,640 | 1/1972 | Huber | 530/401 |
| 3,758,682 | 9/1973 | Huber et al. | 514/21 |
| 4,022,888 | 5/1977 | Huber et al. | 514/21 |
| 4,563,349 | 1/1986 | Miyata et al. | 424/94 |
| 5,438,040 | 8/1995 | Ekwuribe | 514/3 |
| 5,464,614 | 11/1995 | Meyer | 424/94.3 |
| 5,629,015 | 5/1997 | Ribier et al. | 424/450 |
| 5,730,969 | 3/1998 | Hora et al. | 424/85.1 |
| 5,834,013 | 11/1998 | Ribeier et al. | 424/450 |
| 5,846,732 | 12/1998 | Collin et al. | 435/7.1 |

FOREIGN PATENT DOCUMENTS 4248896  9/1992  Japan.

OTHER PUBLICATIONS

Steinman, "Development of Antigen–specific Therapies for Autoimmune Disease", Mol. Biol. Med., vol. 7, pp. 333–339 (1990).

Mohapatra et al., "In Pursuit Of The "Holy Grail": Recombinant Allergens And Peptides As Catalysts For The Allergen–Specific Immunotherapy,", Allergy, vol. 50 (suppl 25), pp. 37–44 (1995).

Adorini et al., "Approaches Toward Peptide–Based Immunotherapy of Autoimmune Diseases", Springer Seminars in Immunopathology, vol. 14, pp. 187–199 (1992).

Burnham, "Polymers For Delivering Peptides and Proteins", Am. J. Hosp. Pharm., vol. 51, pp. 210–218 (1994).

Xian et al., "Degradation Of IGF–I In The Adult Rat Gastrointentinal Tract Is Limited By A Specific Antiserum Or The Dietary Protein Casein", Journal of Endocrinology, vol. 146, pp. 215–225 (1995).

Kitchen, B.J., Dev. Dairy Chemistry, vol. 3, "Indegenous Milk Enzymes", pp. 239–279, 1985.

*Primary Examiner*—Jon P. Weber
*Attorney, Agent, or Firm*—McKenna & Cuneo LLP.

[57] ABSTRACT

A stabilized superoxide dismutase (SOD) peptide is described in which SOD is protected against premature proteolytic degradation by fragments of casein. The stabilized SOD is achieved by mixing the fragments of casein with SOD. The stabilized SOD is incorporated into a composition for oral ingestion by a mammalian patient, whereby the SOD enters the circulatory system and scavenges free radicals present in the body of the patient.

13 Claims, No Drawings

SUPEROXIDE DISMUTASE STABILIZED WITH FRAGMENTS OF CASEIN AND PHARMACEUTICAL COMPOSITIONS INCORPORATING SAME

This nonprovisional application claims the benefits of U.S. Provisional Application No. 60/032,396 filed Dec. 11, 1996.

BACKGROUND OF THE INVENTION

1. Field of the Invention

This invention relates to a method of stabilizing the peptide superoxide dismutase with fragments of casein. This invention further relates to pharmaceutical compositions containing the stabilized superoxide dismutase, and a method of scavenging free radicals from a mammalian body by introducing the pharmaceutical composition into the body orally.

2. Discussion of Related Art

The use of peptides in therapeutic applications has been studied in recent years. See, for example, Steinman, "Development of Antigen-specific Therapies for Autoimmune Disease", Mol. Biol. Med., vol. 7, pps. 333–339 (1990), Mohapatra et al. "In Pursuit of the 'Holy Grail': Recombinant Allergens and Peptides as Catalysts for the Allergen-specific Immunotherapy", Allergy, vol. 50 (suppl 25), pps. 37–44 (1995), and Adorini et al., "Approaches Toward Peptide-based Immunotherapy of Autoimmune Diseases", Springer Seminars in Immunopathology, vol. 14, pps. 187–199 (1992).

Superoxide dismutase (SOD) is a peptide known to act as a scavenger of free radicals, in particular the superoxide radical $O_2^-$, in a mammalian body. See, for example, Burnham, "Polymers for Delivering Peptides and Proteins", Am. J. Hosp. Pharm., vol. 51, pps. 210–218 (1994). As discussed in that article, the level of oxygen free radicals present in a mammalian body increases during times of stress on the body, for example as a result of lung diseases, thermal injury, ischemia and repurfusion, inflammation and organ transplantation, likely as a result of the body not being able to produce sufficient levels of SOD. The level of oxygen free radicals present in the body also increases gradually as the body ages, again likely due to the gradual decrease in SOD production with aging. Increased levels of oxygen free radicals within a mammalian system is dangerous in that these radicals are known to damage a variety of body tissues, for example by attacking and bursting healthy cells.

To combat increased levels of oxygen free radicals in the mammalian system, treatments with SOD are known. See, for example, Burnham, supra at p. 215. Such methods introduce the SOD into the body via injection, that is, directly into the veins or muscles of the body. This is because SOD is very susceptible to attack and breakdown by proteases present in the digestive tract and in the circulatory system of mammalian bodies, thereby greatly reducing the effectiveness of oral administrations of SOD. Native SOD has a half-life on the order of only 10–40 minutes, and thus is typically injected into a mammal in an effort to maximize the scavenging efficiency of SOD prior to breakdown.

Burnham, supra, proposes a method of increasing the half-life of various proteins and peptides, including SOD, by binding a polymer, in particular polyethylene glycol, to the sites of the molecule that cause the body to recognize the molecule as foreign and thus break it down. Burnham acknowledges that the polymers decrease the biological activity of the protein or peptide, but at the same time greatly increase the half-life of the molecule. Burnham does not disclose oral ingestion of SOD compositions.

Xian et al. "Degradation of IGF-I in the Adult Rat Gastrointestinal Tract is Limited by a Specific Antiserum or the Dietary Protein Casein", Journal of Endocrinology, vol. 146, pps. 215–225 (1995), proposes a method of protecting orally ingested IGF-I against proteolytic degradation prior to the peptide being taken up and acting to stimulate gut growth and repair. The peptide was protected effectively in the stomach and colon of rats prior to take up in the intestines by either complexing the peptide with an IGF-I antiserum, or by complexing the peptide with very high concentrations of the whole proteins casein, BSA or lactoferrin.

SUMMARY OF THE INVENTION

It is an object of the present invention to develop a stabilized superoxide dismutase (SOD), and a method of making same, that exhibits an increased half-life over native or pure SOD and an increased resistance to proteolytic degradation. It is a further object of this invention to develop a pharmaceutical composition containing the stabilized SOD and capable of oral administration.

It is a still further object of this invention to develop a method of orally introducing SOD into a mammalian body, wherein the SOD contained in the oral dose may be lowered. Such lowering of the SOD amount in the composition should be possible due to the SOD being less susceptible to proteolytic degradation in the digestive tract and in the circulatory system following absorption from the intestine of the mammal.

These and other objects are achieved by the present invention, wherein superoxide dismutase (SOD) is stabilized by fragments of casein. The stabilized SOD forms kernels which are readily incorporated into a pharmaceutical composition containing a pharmaceutically acceptable carrier.

When the composition is orally ingested by a mammal, the stabilized SOD is less susceptible to proteolytic degradation in the digestive tract and circulatory system of the mammal. The stabilized SOD thus exhibits an increased half-life over native SOD, and is thus more effective in scavenging free radicals from the mammalian body. The composition also exhibits an increased absorption rate from the intestine into the circulatory system of the mammal. As a result of the above, the composition may contain lower levels of stabilized SOD.

DETAILED DESCRIPTION OF PREFERRED EMBODIMENTS

SOD is very susceptible to rapid degradation by proteases. Proteases are present in the digestive tract and circulatory system of mammals, including humans. SOD has numerous sites throughout the peptide chain that are susceptible to degradation by proteases. Such proteases include, for example, pepsin, trypsin, chymotrypsin, and the like. These sites of SOD are hereinafter referred to as "proteolytic degradation susceptible sites". These sites permit proteases to attack and breakdown the peptide, thereby rendering it unable to scavenge free radicals in the body, and eventually eliminating it from the body.

In mammalian digestion, matter ingested is delivered to the stomach, where digestive enzymes and gastric juices are secreted. The solution then passes to the intestine, where additional enzymes are introduced to further the digestion process. Digested matter is absorbed by the intestinal wall and introduced into the circulatory system or bloodstream. Undigested matter is eliminated.

If SOD were orally ingested in its native or pure form, the SOD would be rapidly degraded by the proteases and enzymes in the digestive tract. The small amount of original SOD that remained intact to be absorbed into the circulatory system would be still further subjected to degradation from proteases present in plasma/blood. SOD injected into the blood has a half-life on the order of 10–40 minutes, and less if orally ingested. Little, if any, SOD would remain resident in the circulatory system for a long enough period to scavenge free radicals from the body.

In order for orally ingested SOD to survive proteolytic degradation for a time sufficient to permit absorption into the circulatory system and delivery through the circulatory system to efficiently and effectively scavenge free radicals from the body, the proteolytic degradation susceptible sites of the SOD are protected. The protective material comprises fragments of casein. Casein is a protein commonly found in milk. Randomly cleaved fragments of this protein are commercially available. For example, Amicase™ is an acid-hydrolyzed bovine casein available from several vendors such as Sigma Chemical.

Stabilizing the SOD with fragments of casein has several advantages over stabilizing the peptide with the entire casein protein. First, entire casein proteins will not effectively protect all of the proteolytic degradation susceptible sites of the SOD. Only some of the sites will be protected, and the bulkiness of the casein will prevent additional casein from being able to protect the unprotected sites. Although this problem may be somewhat alleviated by adding excessive amounts of casein, such becomes inefficient and cost prohibitive.

On the other hand, fragments of casein are much shorter in chain length than the entire protein. As such, the fragments are able to effectively protect (i.e., stabilize) a substantial majority, if not all, of the proteolytic degradation susceptible sites of SOD. Sites left unprotected by one fragment are protected by another fragment because the less bulky fragments do not interfere with one another to prevent other fragments from protecting unprotected sites.

An additional advantage is that because the fragments more effectively protect the peptide, much lower amounts of the fragments are needed compared to amounts of the entire casein protein. Furthermore, although not yet substantiated by clinical evidence, it is also believed that the fragments of casein provide an additional benefit of improving the rate of absorption of the stabilized SOD into the circulatory system.

The casein fragments stabilize the SOD by forming multiple overlapping layers or strata upon the SOD. The casein fragments are not chemically bonded to SOD, but instead are attracted to SOD through various interacting physical forces, including hydrophobic interaction, hydrogen bonding and van der Waals' forces. The casein fragments protect the SOD against proteolytic degradation in that proteases must first attack and breakdown the casein fragments before they can reach the SOD and break it down, thereby prolonging the biological integrity of SOD within the mammalian body. The half-life of the stabilized SOD is increased up to at least, for example, 50 minutes, and is more preferably increased to 90 minutes or more. Thus, a majority of the stabilized SOD orally ingested survives the digestive tract intact to be absorbed into the circulatory system, and there survives a sufficient time to effectively scavenge free radicals present in the body.

The stabilized SOD is made by physically mixing pure SOD with the fragments of casein. Any suitable commercially available mechanical mixing device may be used. The components may be introduced in any order. The molar ratio of fragments of casein to SOD is, for example, 1.0–3.0:1.0, preferably 1.0–2.0:1.0, more preferably 1.0–1.5:1.0. Following mixing for a period of time sufficient to effect protection of the SOD, for example mixing of 5 minutes or more, the stabilized SOD is derived.

For oral ingestion, the stabilized SOD is incorporated into a pharmaceutically acceptable carrier to form a pharmaceutical composition. The composition may be in either solid or liquid form, depending on the carrier selected.

Solid form preparations include, for example, powders, tablets, dispersible granules and capsules. A solid carrier can be one or more substances which may also act as diluents, flavoring agents, solubilizers, lubricants, suspending agents, binders, tablet disintegrating agents, or encapsulating materials. Suitable carrier materials known in the pharmaceutical art include, for example, magnesium carbonate, calcium carbonate, sodium bicarbonate, magnesium stearate, calcium stearate, talc, lactose, sugar, pectin, dextrin, starch, tragacanth, cellulose derivatives, methyl cellulose, sodium carboxymethyl cellulose, a low-melting wax, cocoa butter, alginates gelatin polyvinyl pyrrolidone, polyethyl glycols, quaternary ammonium compounds, and the like.

In tablets, the carrier is a finely divided solid which is in a mixture with the stabilized SOD. The stabilized SOD is mixed with the carrier having the necessary binding properties in suitable proportions and compacted in the shape and size desired.

In capsules, the stabilized SOD is encapsulated with an encapsulating material as a carrier, thereby providing a capsule in which the stabilized SOD (with or without other carriers) is surrounded by a carrier.

Liquid form preparations include solutions, suspensions, and emulsions. Aqueous solutions for oral administration can be prepared by dissolving the stabilized SOD in water and adding suitable colorants, flavoring agents, stabilizers, and thickening agents as desired. Aqueous suspensions for oral use can be made by dispersing the stabilized SOD in water together with a viscous material such as natural synthetic gums, resins, methyl cellulose, sodium carboxymethyl cellulose, and other suspending agents known to the pharmaceutical art.

The stabilized SOD is contained in the pharmaceutical composition in an amount of, for example, 10–40 percent by weight of the composition, more preferably 20–30 percent by weight of the composition, most preferably 25 percent by weight of the composition.

In a preferred embodiment, the pharmaceutical composition also includes Polygonum multiflorum, commonly also referred to as fo-ti. Fo-ti is an herb of Chinese origin derived from the root of the Polygonum multiflorum. Studies have revealed that fo-ti increases the activity of SOD, among other properties. See, for example, Xiao, "Immunological Aspects of Chinese Medicinal Plants as Antiageing Drugs", Journal of Ethnopharmacology, vol. 38, pps. 167–175 (1993). If present, fo-ti is preferably present in the composition in an amount of from, for example, 5 to 20 percent by weight of the composition, preferably 10 to 15 percent by weight of the composition. Fo-ti is added preferably by admixing with the carrier and stabilized SOD.

The pharmaceutical composition is preferably administered to a mammal orally. In order to provide effective free radical scavenging, an oral dose in tablet form of two tablets per day, wherein each tablet contains, for example, from 200–300 mg, preferably 250 mg, of stabilized SOD, is possible. Preferred daily dose levels preferably range from 200–1,000 mg, for example. However, the exact dosage level may vary as understood in the art depending upon the patient's weight, the size of the solid dose form (e.g., tablet), the amount of stabilized SOD contained in the dose form, etc.

The invention has been described in detail with particular reference to preferred embodiments thereof. However, it will be appreciated that those skilled in the art, upon consideration of this disclosure, may make variations and modifications within the spirit and scope of the invention.

What is claimed is:

1. A pharmaceutical composition comprising stabilized superoxide dismutase, wherein proteolytic degradation susceptible sites of the superoxide dismutase are protected with fragments of casein and wherein the stabilized superoxide dismutase is present in an amount of from 10 to 40 percent by weight of the composition, and a pharmaceutically acceptable carrier.

2. A pharmaceutical composition according to claim 1, wherein the stabilized superoxide dismutase is present in an amount of from 20 to 30 percent by weight of the composition.

3. A pharmaceutical composition according to claim 1, wherein the pharmaceutical composition is in solid or liquid form.

4. A pharmaceutical composition according to claim 3, wherein the pharmaceutical composition is in solid form and the carrier comprises one or more of diluents, flavoring agents, solubilizers, lubricants, suspending agents, binders, disintegrating agents or encapsulating materials.

5. A pharmaceutical composition according to claim 4, wherein the pharmaceutical composition comprises a tablet.

6. A pharmaceutical composition according to claim 1, wherein the pharmaceutical composition further comprises Polygonum multiflorum.

7. A pharmaceutical composition according to claim 6, wherein the Polygonum multiflorum is contained in the pharmaceutical composition in an amount of from 5 to 20 percent by weight of the pharmaceutical composition.

8. A method of preparing a pharmaceutical composition according to claim 1, which comprises mixing wuperoxide dismutase, fragments of casein and a pharmaceutically acceptable carrier, whereby proteolytic degradation susceptible sites of the superoxide dismutase are protected by the fragments of casein.

9. A method according to claim 8, wherein the fragments of casein and the superoxide dismutase are mixed in a ration of 1.0-2.0:1.0.

10. A method according to claim 8, wherein the fragments of casein and the superoxide dismutase are mixed in a ration of 1.0-1.5:1.0.

11. A method of scavenging free radicals from a mammalian body, comprising orally introducing into the mammalian body a pharmaceutical composition according to claim 1.

12. A method according to claim 11, wherein the daily dose orally introduced into the mammalian body is from 200 to 1,000 mg.

13. A method according to claim 11, wherein the pharmaceutical composition is in the form of a tablet, and each tablet contains from 200 to 300 mg of the stabilized superoxide dismutase.

* * * * *

UNITED STATES PATENT AND TRADEMARK OFFICE
CERTIFICATE OF CORRECTION

PATENT NO. : 6,132,712
DATED : 17 October 2000
INVENTOR(S) : A. Glen Braswell et al.

It is certified that error appears in the above-identified patent and that said Letters Patent is hereby corrected as shown below:

<u>In the Claims</u>:

Column 6, Claim 8, Line 2 change "wuperoxide" to --superoxide--;

Column 6, Claim 9, Line 2 change "ration" to --ratio--;

Column 6, Claim 10, Line 2 change "ration" to --ratio--.

Signed and Sealed this

Eighth Day of May, 2001

*Attest:*

NICHOLAS P. GODICI

*Attesting Officer*     Acting Director of the United States Patent and Trademark Office